(12) United States Patent
Benner

(10) Patent No.: US 10,091,578 B2
(45) Date of Patent: Oct. 2, 2018

(54) METHOD FOR ADJUSTING A VOLUME LEVEL OF A COMMUNICATIONS UNIT AND A COMMUNICATIONS UNIT

(71) Applicant: Thomas Benner, Erlangen (DE)

(72) Inventor: Thomas Benner, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 57 days.

(21) Appl. No.: 14/806,156

(22) Filed: Jul. 22, 2015

(65) Prior Publication Data

US 2016/0029135 A1 Jan. 28, 2016

(30) Foreign Application Priority Data

Jul. 22, 2014 (DE) ........................ 10 2014 214 265

(51) Int. Cl.
*H04R 3/00* (2006.01)
*G10K 11/16* (2006.01)
(Continued)

(52) U.S. Cl.
CPC ............... *H04R 3/00* (2013.01); *A61B 5/055* (2013.01); *A61B 5/7465* (2013.01);
(Continued)

(58) Field of Classification Search
CPC ..... A61B 5/055; A61B 5/0024; A61B 5/7465; A61B 2560/0242; G06F 19/3406;
(Continued)

(56) References Cited

U.S. PATENT DOCUMENTS

| | | | | |
|---|---|---|---|---|
| 4,903,703 A * | 2/1990 | Igarashi | ................... | H04R 1/46 381/151 |
| 4,981,137 A * | 1/1991 | Kondo | ................... | A61B 5/055 324/318 |
| 5,313,945 A * | 5/1994 | Friedlander | ........ | G01R 33/3854 324/318 |
| 5,384,537 A * | 1/1995 | Ito | ........................ | G01R 33/283 381/94.2 |
| 8,085,942 B2 * | 12/2011 | Rasmussen | ............ | A61B 5/055 381/71.1 |
| 2002/0071573 A1 * | 6/2002 | Finn | ..................... | G10L 21/0208 381/93 |
| 2003/0071624 A1 * | 4/2003 | Schwarz | .............. | G01R 33/283 324/318 |

(Continued)

FOREIGN PATENT DOCUMENTS

EP 2095144 B1 9/2009
JP 2000339000 A 12/2000
(Continued)

OTHER PUBLICATIONS

German Office Action for related German Application No. 10 2014 214 265.2, dated Apr. 20, 2015, with English Translation.

*Primary Examiner* — Thang Tran
(74) *Attorney, Agent, or Firm* — Lempia Summerfield Katz LLC

(57) ABSTRACT

A method for adjusting a volume level of a communications unit is provided. The communications unit is configured for communication between a medical operator and a patient during a magnetic resonance examination and includes at least one microphone and at least one loudspeaker. The method includes detecting communication signals by the at least one microphone, transmitting the detected communication signals to the at least one loudspeaker, and an acoustic output of the detected communication signals by the at least one loudspeaker. A volume level of the at least one microphone may be automatically adjusted during detection of the communication signals, and/or a volume level of the at least one loudspeaker may be automatically adjusted during the acoustic output of the communication signals.

15 Claims, 1 Drawing Sheet

(51) Int. Cl.
  *A61B 5/055* (2006.01)
  *G10K 11/175* (2006.01)
  *A61B 5/00* (2006.01)

(52) U.S. Cl.
  CPC .... *G10K 11/175* (2013.01); *G10K 2210/1161* (2013.01); *H04R 2227/001* (2013.01); *H04R 2430/01* (2013.01)

(58) Field of Classification Search
  CPC .......... G10K 2210/1161; G10K 11/175; G06T 2207/10088; G01R 33/288; G01R 33/283; G01R 33/543; G10L 21/0208; G10L 21/0232; H04R 1/1083; H04R 1/46; H04R 3/00; H04R 3/005; H04R 3/02; H04R 2430/01; H04R 2227/001
  See application file for complete search history.

(56) References Cited

U.S. PATENT DOCUMENTS

| | | | |
|---|---|---|---|
| 2008/0118077 A1 | 5/2008 | Rasmussen | |
| 2009/0067615 A1* | 3/2009 | Strandberg | H04M 9/082 379/406.01 |
| 2011/0268293 A1* | 11/2011 | Mantegna | H03G 3/32 381/103 |

FOREIGN PATENT DOCUMENTS

| | | |
|---|---|---|
| JP | 2009195649 A | 9/2009 |
| WO | WO2010055283 A1 | 5/2010 |

\* cited by examiner

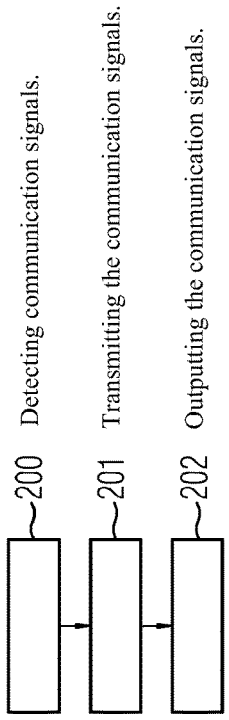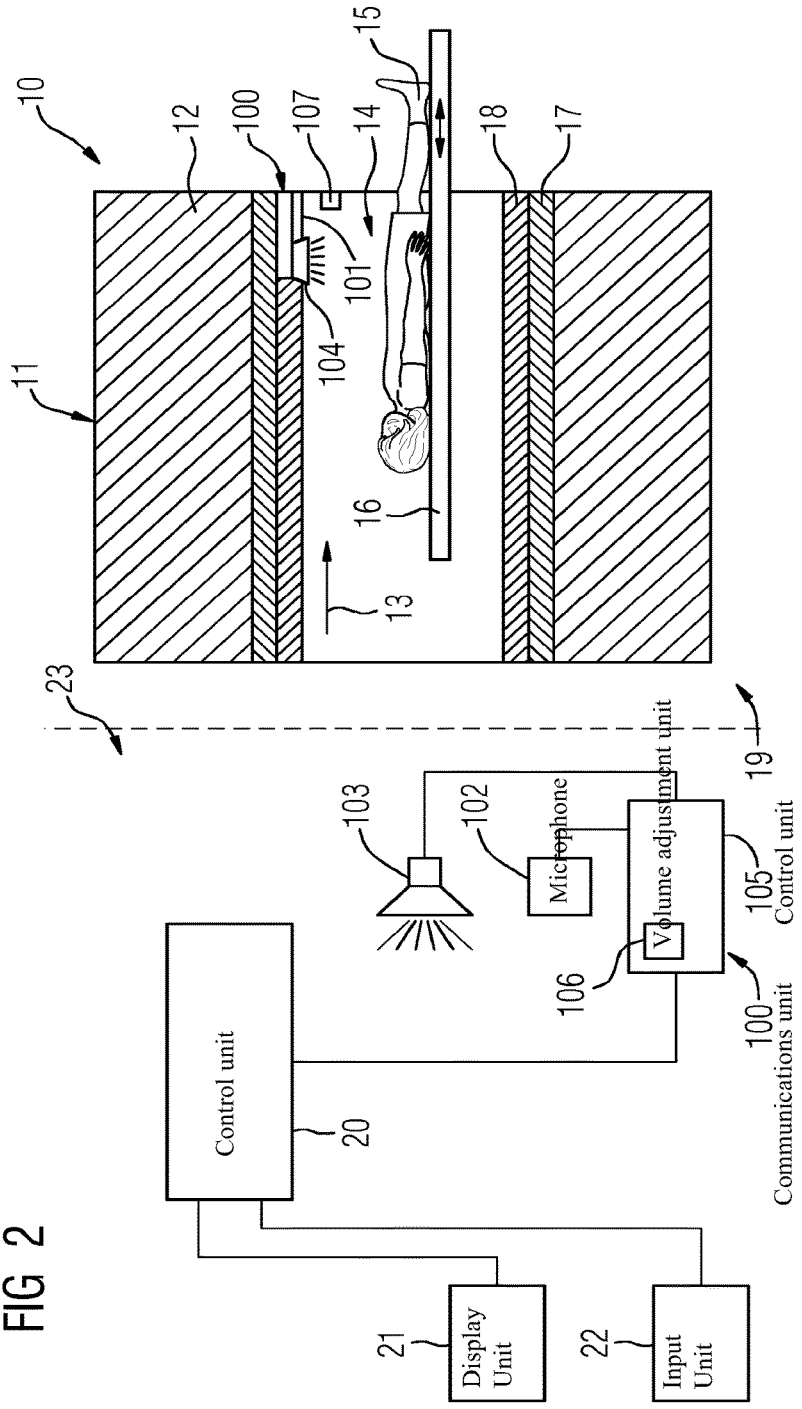

METHOD FOR ADJUSTING A VOLUME LEVEL OF A COMMUNICATIONS UNIT AND A COMMUNICATIONS UNIT

This application claims the benefit of DE 10 2014 214 265.2, filed on Jul. 22, 2014, which is hereby incorporated by reference in its entirety.

BACKGROUND

The present embodiments relate to adjusting a volume level of a communications unit.

During a magnetic resonance examination, it is important that there is communication between the patient, who is arranged for the magnetic resonance examination at least partially inside a patient examination region of a magnetic resonance device, and a medical operator in charge of the magnetic resonance examination, who may be in a control room during the magnetic resonance examination. The patient may inform the medical operator, for example, of his/her current condition hereby. The medical operator may also give instructions to the patient during the magnetic resonance examination (e.g., in the form of breathing commands and/or specific position instructions for the positioning of individual regions of the body of the patient for the magnetic resonance examination).

Communication between the patient and the medical operator occurs using a communications unit, which, in the vicinity of the patient (e.g., on the magnetic resonance device), has a microphone and a loudspeaker and in the vicinity of the medical operator (e.g., inside the control room), has a microphone and a loudspeaker.

During a magnetic resonance examination, a volume level is, however, partially (e.g., in the vicinity of the magnetic resonance device) so high that communication between the patient and the medical operator is barely still possible. Due to the loud noises caused by the gradient coils during a recording time of magnetic resonance data (e.g., the noises produced by the gradient coils) are transferred to the medical operator by the microphone arranged in the vicinity of the patient.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a method and a device for communication between a patient and a medical operator that easily enable transmission of undesirable interference noises during a recording time of magnetic resonance data to be reduced are provided.

A method for adjusting a volume level of a communications unit is provided. The communications unit is configured for communication between a medical operator and a patient during a magnetic resonance examination and has at least one microphone and at least one loudspeaker. The method includes detection of communication signals by the at least one microphone, transmitting the detected communication signals to the at least one loudspeaker, and an acoustic output of the detected communication signals by the at least one loudspeaker.

A volume level of the at least one microphone may be automatically adjusted during detection of the communication signals, and/or a volume level of the at least one loudspeaker may be automatically adjusted during the acoustic output of the communication signals.

Loud interference noises, which are produced during magnetic resonance scans by the gradient coils of a magnetic resonance device, may be reduced and/or eliminated easily in this way, inside the communications unit during a magnetic resonance recording time. For example, the transmission of undesirable interference noises during the recording time of magnetic resonance data may be reduced and/or prevented. Laborious manual adjustment of the volume level by the medical operator, in which the medical operator switches off the at least one microphone and/or the at least one loudspeaker and switches the at least one microphone and/or the at least one loudspeaker on again as a function of background noise of the magnetic resonance device, may also be avoided in this way during the magnetic resonance scan. The workflow of the medical operator may be simplified thereby. The adjustment of the volume level of the at least one microphone and/or of the at least one loudspeaker may include both a reduction in the volume level and an increase in the volume level.

The communications unit may have a first microphone that is arranged in the vicinity of the patient during the magnetic resonance examination (e.g., inside the examination region of the magnetic resonance device). This first microphone is configured to detect speech signals and/or further communication signals of the patient during the magnetic resonance examination. The communications unit also includes a second microphone that is arranged inside a control room, in which the medical operator is located. This second microphone is configured to detect speech signals and/or further communication signals of the medical operator. Undesirable noises, which are produced by the magnetic resonance device (e.g., the gradient coils), are also detected by the first microphone during the magnetic resonance scan, so detection of these undesirable noises and therewith also transmission of these noises into the control room may be prevented by the automatic adjustment of the volume level at the first microphone.

The communications unit may include a first loudspeaker that is arranged inside the control room. This first loudspeaker is configured for acoustic output of speech signals and/or further communication signals to the medical operator. The communications unit also includes a second loudspeaker that is arranged in the vicinity of the patient during the magnetic resonance examination (e.g., inside the examination region of the magnetic resonance device). This second loudspeaker is configured for acoustic output of speech signals and/or further communication signals to the patient during the magnetic resonance examination. The communication signals detected by the first microphone and also noises are introduced into the control room by the first loudspeaker, so an output of these undesirable noises may be prevented by the automatic adjustment of the volume level to the first loudspeaker.

The automatic adjustment of the volume level may only be provided in the first microphone and/or the first loudspeaker since only the first microphone and the first loudspeaker contribute to a transmission of the loud interference noises during the magnetic resonance scans from a measuring room, in which the magnetic resonance device is arranged, into the control room. A transmission of speech signals and/or further communication signals from the control room into the measuring room by the second microphone and the second loudspeaker may therefore continue to be possible unrestrictedly. However, in an alternative embodiment, automatic adjustment of a volume level at the second microphone and/or the second loudspeaker of the communications unit may also be provided.

In this connection, communication signals may, for example, be signals that are detected and/or output by the communications unit. By this, communication occurs between the patient and the medical operator. By way of example, the communication signals may include speech signals detected by the first microphone and/or by the second microphone. For automatic adjustment of the volume level, the communications unit may include a volume adjustment unit configured for adjustment of the volume level of the first microphone and/or of the first loudspeaker. In this connection, a volume level of the at least one microphone may, for example, be a sensitivity and/or a sensitivity value of the at least one microphone. With this, communication signals and/or further noises are detected in the vicinity of the microphone. A volume level of the at least one loudspeaker may, for example, be a volume and/or a volume level with which communication signals are acoustically output by the at least one loudspeaker.

In a further embodiment, the volume level is adjusted as a function of a time parameter of a magnetic resonance scan. The time parameter of a magnetic resonance scan may include a start time and/or an end time of the magnetic resonance scan. A reduction in the volume level may be activated in this way at the beginning of the magnetic resonance scan, and this reduction may be deactivated again at the end of the magnetic resonance scan. After the magnetic resonance scan, communication at a normal volume is thus possible again from the measuring room into the control room (e.g., from the patient to the medical operator). Accidentally forgetting to manually deactivate the reduction in the volume level may be advantageously prevented, and therewith, an ideal volume level may always be adjusted by the volume adjustment unit. A magnetic resonance examination may include a plurality of magnetic resonance scans. The beginning (e.g., the start time) and/or the end (e.g., the end time) of the magnetic resonance scan may advantageously be determined by a system control unit and be transmitted to the communications unit. In one embodiment, the beginning (e.g., the start time) and/or the end (e.g., the end time) of the magnetic resonance scan are input manually by the medical operator and/or detected directly by the communications unit.

An ambient volume level is detected by a volume measurement, with the volume level being adjusted as a function of the measured ambient volume level of the volume measurement. A volume level of the surroundings of the at least one microphone and/or of the at least one loudspeaker that is always current may be advantageously detected in this way, and therewith, an ideal adjustment of the volume level of the at least one microphone during detection of the communication signals and/or an ideal adjustment of the volume level of the at least one loudspeaker during the acoustic output of the communication signals may be achieved. An undesirable misadjustment of the volume level of the at least one microphone during detection of communication signals and/or of the volume level of the at least one loudspeaker during the acoustic output of communication signals may be advantageously prevented in this way.

The volume level may also be adjusted particularly advantageously in this way as a function of a relation of the measured ambient volume level with respect to a reference value and/or threshold value. In one embodiment, as soon as the measured ambient volume level exceeds the reference value and/or threshold value, the volume level is automatically adjusted (e.g., there is a reduction in the volume level of the at least one microphone during detection of the communication signals and/or of the at least one loudspeaker during the acoustic output of the communication signals). The volume level may be automatically increased in this way as soon as the measured ambient volume level falls below the reference value and/or threshold value. An individual noise level may be ascertained in this way by the reference value, up to which the transmitted interference noises from the measuring room are still tolerable for the medical operator inside the control room. Two or more different reference values and/or threshold values may also be ascertained in this way. A different adjustment value for adjustment of the volume level of the at least one microphone and/or of the at least one loudspeaker.

A particularly compact and inexpensive communications unit may be achieved if the volume measurement for detection of the ambient volume level occurs by the at least one microphone. Further detection units may advantageously be dispensed with in this way. Alternatively or additionally, the volume may be measured by a separate volume detection unit, whereby a volume measurement that is independent of a communication signal transmission may occur.

The adjustment of the volume level of the at least one microphone during detection of the communication signals and/or the adjustment of the volume level of the at least one loudspeaker during the output of the detected communication signals includes a deactivation of the volume level. An effective suppression of a transmission of the interference noises present inside the measuring room, which are caused by the gradient coils, may be achieved particularly easily in this way. In this connection, a deactivation of the volume level may be a setting of the volume level to a value "0" and/or a muting of the at least one microphone and/or of the at least one loudspeaker. For example, transmission of communication signals and/or noises between the at least one microphone, which is arranged in the measuring room, to the at least one loudspeaker, which is arranged in the control room, may be prevented in this way. Alternatively or additionally, an acoustic output of communication signals by the at least one loudspeaker may be prevented. The volume level may be deactivated as a function of a detected ambient volume and/or a time parameter of the magnetic resonance scan.

In one embodiment, the adjustment of the volume level of the at least one microphone during detection of the communication signals and/or the adjustment of the volume level of the at least one loudspeaker during an output of the detected communication signals includes an adjustment of the volume level to an ambient volume level of the at least one microphone and/or of the at least one loudspeaker. The volume level of the at least one microphone and/or of the at least one loudspeaker may be adapted to an ambient noise hereby. By way of example, a sensitivity of the microphone may be reduced in this connection by the adjustment of the volume level, for example, with the onset of an interference noise, or the sensitivity of the microphone may also be increased, for example, with the cessation of an interfering noise source inside the measuring room. Alternatively or additionally, the volume level of the loudspeaker may be reduced, for example, with the onset of an interference noise, or increased (e.g., with the cessation of the interfering noise source).

The ambient volume level may occur in this connection via a measurement and/or detection of a volume level of the surroundings of the at least one microphone and/or of the at least one loudspeaker. In one embodiment, the ambient volume level may be determined using a start time of a magnetic resonance scan or an end time of the magnetic resonance scan.

The ambient volume level is calculated for the magnetic resonance scan. The volume level may be adjusted in this way to an ambient noise of the at least one microphone and/or of the at least one loudspeaker without additional measuring and/or detection of the ambient volume level. The ambient volume level may be calculated by way of example using a gradient wave form for an adjusted gradient sequence of the magnetic resonance scan (e.g., the pending magnetic resonance scan), so a current ambient volume level for the magnetic resonance scan is available for the adjustment of the volume level as early as at the beginning of the magnetic resonance scan.

In an embodiment, after a cessation of interference noises and/or the end of a magnetic resonance scan, the volume level is automatically set to an original volume level. In this way, bidirectional communication between the patient and the medical operator may be started again in a break in the examination and/or between two magnetic resonance scans. For example, the patient may communicate desires and/or sensitivities to the medical operator again unrestrictedly.

In one embodiment, a communications unit includes at least one microphone, at least one loudspeaker and a control unit. The communications unit is configured for communication between a medical operator and a patient during a magnetic resonance examination.

The control unit includes a volume adjustment unit configured to carry out a method for adjusting a volume level of the communications unit. The method includes detecting communication signals by the at least one microphone, transmitting the detected communication signals to the at least one loudspeaker, and an acoustic output of the detected communication signals by the at least one loudspeaker. A volume level of the at least one microphone during detection of the communication signals and/or a volume level of the at least one loudspeaker during the acoustic output of the communication signals may be automatically adjusted by the volume adjustment unit.

Loud interference noises, which are produced during magnetic resonance scans by the gradient coils of a magnetic resonance device, may advantageously be reduced and/or eliminated particularly easily in this way inside the communications unit during a magnetic resonance recording time. For example, the volume level of the at least one microphone and/or the at least one loudspeaker may be automatically adjusted in this way by the volume adjustment unit to an ambient volume and/or to a time parameter of the magnetic resonance scan. A complex manual adjustment of the volume level by the medical operator, in which the medical operator switches off the at least one microphone and/or the at least one loudspeaker and switches the at least one microphone and/or the at least one loudspeaker on again as a function of background noise of the magnetic resonance device, may be avoided during the magnetic resonance scan. A workflow of the medical operator may be simplified thereby.

The advantages of the communications unit of one or more of the present embodiments substantially match the advantages of the method for adjusting a volume level of a communications unit of one or more of the present embodiments. These have been stated above in detail. Features, advantages or alternative embodiments mentioned in this connection may likewise be transferred to the other subject matters and vice versa.

In one embodiment, the communications unit includes a volume detection unit. An adjustment of the volume level to a current volume of the surroundings of the at least one microphone and/or of the at least one loudspeaker may advantageously be made in this way. The volume detection unit may be formed by a separate volume detection unit, which is constructed separately to the at least one microphone and/or the at least one loudspeaker. As an alternative to this, an embodiment of the at least one microphone as a volume detection unit may also be provided, so a particularly compact communications unit may be provided.

In one embodiment, a magnetic resonance device includes a communications unit that includes at least one microphone, at least one loudspeaker and a control unit. The communications unit is configured for communication between a medical operator and a patient during a magnetic resonance examination. The control unit includes a volume adjustment unit configured to carry out a method for adjusting a volume level of a communications unit. The method includes detecting communication signals by the at least one microphone, transmitting the detected communication signals to the at least one loudspeaker, and an acoustic output of the detected communication signals by the at least one loudspeaker. A volume level of the at least one microphone during detection of the communication signals and/or a volume level of the at least one loudspeaker during the acoustic output of the communication signals may be automatically adjusted.

The advantages of the magnetic resonance device of one or more of the present embodiments substantially match the advantages of the communications unit of one or more of the present embodiments and/or of the method for adjusting a volume level of a communications unit of one or more of the present embodiments. These have been stated above in detail. Features, advantages or alternative embodiments mentioned in this connection may likewise be transferred to the other subject matters and vice versa.

In one embodiment, a computer program product that includes a program and may be loaded directly into a memory (e.g., a non-transitory computer-readable storage medium) of a programmable control unit (e.g., including one or more processors) of a communications unit is provided. The program includes instructions executable by the one or more processors to adjust a volume of a communications unit if the program is run in the control unit of the communications unit.

BRIEF DESCRIPTION OF THE DRAWINGS

FIG. 1 shows one embodiment of a method for adjusting a volume level of a communications unit; and FIG. 2 shows one embodiment of a magnetic resonance device having a communications unit in a schematic diagram.

DETAILED DESCRIPTION

FIG. 2 schematically shows one embodiment of a magnetic resonance device 10. The magnetic resonance device 10 includes a magnetic unit 11 including a superconducting main magnet 12 for generating a strong and, for example, constant main magnetic field 13. The magnetic resonance device 10 includes a patient-receiving region 14 for receiving a patient 15. The patient-receiving region 14 in the present exemplary embodiment is cylindrical and cylindrically surrounded in a circumferential direction by the magnetic unit 11. Other designs of the patient-receiving region 14 different from this, however, may be provided. The patient 15 may be pushed by a patient positioning device 16 of the magnetic resonance device 10 into the patient-receiving region 14.

The magnetic unit 11 also includes a gradient coil unit 17 for generating magnetic field gradients that are used for spatial encoding during imaging. The magnetic unit 11 also includes a high-frequency antenna unit 18 for exciting a polarization that is established in the main magnetic field 13 generated by the main magnet 12. The magnetic unit 11 is arranged inside a measuring room 19 (e.g., a magnetic resonance room).

To control the magnetic unit 11, the magnetic resonance device 10 includes a system control unit 20. The system control unit 20 centrally controls the magnetic resonance device 10 such as, by way of example, the performance of a predetermined imaging gradient echo sequence. The system control unit 20 also includes an evaluation unit (not shown) for evaluating image data. Control information such as, for example, imaging parameters and reconstructed magnetic resonance images may be displayed on a display unit 21 (e.g., on at least one monitor) of the magnetic resonance device 10 for a medical operator. The magnetic resonance device 10 includes an input unit 22, by which information and/or parameters may be input by the medical operator during a measuring process. The system control unit 20 is arranged inside a control room 23 that is independent of the measuring room 19.

The magnetic resonance device 10 also includes a communications unit 100 configured for communication between the patient 15, who for a magnetic resonance examination is arranged inside the measuring room 19 (e.g., inside the patient-receiving region 14 of the magnetic resonance device 10), and the medical operator, who is located inside the control room 23 during the magnetic resonance examination. The communications unit 100 includes at least one microphone 101, 102 and at least one loudspeaker 103, 104. In the present exemplary embodiment, the communications unit 100 includes two microphones 101, 102 and two loudspeakers 103, 104. However, a design of the communications unit 100 that is different from this, having just one microphone or more than two microphones and/or one loudspeaker or more than two loudspeakers, may be provided.

A first microphone of the two microphones 101 is arranged inside the measuring room 19 in the vicinity of the patient 15. The first microphone 101 is arranged in the vicinity of the patient-receiving region 14 (e.g., at an edge of an insertion opening of the patient-receiving region 14). Noises (e.g., communication signals of the patient) inside the measuring room 19 (e.g., inside the patient-receiving region 14) may be detected by the first microphone 101. A second microphone of the two microphones 102 is arranged inside the control room 23. Communication signals of the medical operator inside the control room 23, for example, may be detected by the second microphone 102.

A first of the two loudspeakers 103 is arranged inside the control room 23 in order to emit communication signals into the control room 23. A second of the two loudspeakers 104 is arranged inside the measuring room 19 in the vicinity of the patient 15. The second loudspeaker 104 is arranged in the vicinity of the patient-receiving region 14 (e.g., at an edge of an insertion opening of the patient-receiving region 14). Communication signals may be emitted into the measuring room 19 by the second loudspeaker 104. The second loudspeaker 104 may be integrated inside headphones that the patient 15 wears during the magnetic resonance examination. The first microphone 101 may be integrated on the headphones that the patient 15 wears during the magnetic resonance examination.

During a measurement operation of the magnetic resonance device 10, communication signals may be detected inside the patient-receiving region 14 by the first microphone 101 and may be emitted inside the control room 23 by the first loudspeaker 103, so communication from the patient 15 to the medical operator may occur during the magnetic resonance examination. In a measurement operation of the magnetic resonance device 10, communication signals may be detected inside the control room 23 by the second microphone 102 and may be emitted inside the patient-receiving region 14 by the second loudspeaker 104, so communication from the medical operator to the patient 15 (e.g., in the form of a breathing command and/or further examination instructions) may occur during the magnetic resonance examination.

For data transmission (e.g., for a transmission of communication signal data), the communications unit 100 includes a data transmission unit (not shown). This data transfer unit transfers the communication signals between the control room and the measuring room as well. Data may also be transmitted by the data transfer unit wirelessly and/or in a cable-free manner.

FIG. 1 schematically shows one embodiment of a method for adjusting a volume level of the communications unit 100. The method is carried out by the communications unit 100. For this purpose, the communications unit 100 includes a control unit 105 with a volume adjustment unit 106 and adjustment software and/or evaluation programs necessary for carrying out the method for adjusting a volume level. The volume adjustment unit 106 of the communications unit 100 includes a processor unit (not shown), by which the evaluation software and/or the evaluation programs are run, and a memory unit (not shown), in which the evaluation software and/or the evaluation programs are stored.

In act 200, communication signals are detected by the first microphone 101 inside the patient-receiving region 14. Communication signals are also detected in act 200 by the second microphone 102 inside the control room 23. The detected communication signals are transmitted by the data transmission unit from the first microphone 101 to the first loudspeaker 103 and from the second microphone 102 to the second loudspeaker 104 of the communications unit 100 in act 201. In act 202, the transmitted communication signals are output acoustically by the first loudspeaker 103 into the control room 23 (e.g., emitted) and are output acoustically (e.g., emitted) by the second loudspeaker 104 in the measuring room 19.

A volume level may be adjusted during act 200 of detection of the communication signals by the first microphone 101 and/or during act 202 of the acoustic output of the communication signals by the first loudspeaker 103. The volume level is automatically adjusted in this connection by the volume adjustment unit 106. The volume level of the first microphone 101 may include, for example, a sensitivity and/or a sensitivity value of the first microphone 101 with which communication signals and/or further noises in the surroundings of the first microphone 101 are detected. The volume level of the first loudspeaker 102 may, for example, also include a volume and/or volume level at which communication signals are output acoustically by the first loudspeaker 103.

The volume level may be adjusted during act 200 of detection of the communication signals by the first microphone 101 and/or during act 202 of acoustic output of the communication signals by the first loudspeaker 103 as a function of a time parameter of a magnetic resonance scan of the magnetic resonance examination. The time parameter of the magnetic resonance scan may, for example, include a start time and/or an end time of the magnetic resonance scan. For example, the volume level may be reduced and/or deactivated by the volume adjustment unit 106 at a start time or the beginning of the magnetic resonance scan during act 200 of detection of the communication signals by the first microphone 101 and/or during act 202 of acoustic output of the communication signals by the first loudspeaker 103. If the volume level of the first microphone 101 and/or of the first loudspeaker 103 has already been reduced, the volume level may be re-set to its original value and/or activated again by the volume adjustment unit 106 at an end time or the end of the magnetic resonance scan during act 200 of detection of the communication signals by the first microphone 101 and/or during act 202 of acoustic output of the communication signals by the first loudspeaker 103.

For example, there is an adjustment of the volume level to a value of "0" and/or a muting of the volume of the first microphone 101 and/or of the first loudspeaker 103 by the volume adjustment unit 106 by the deactivation of the volume level. The communications unit 100 may be deactivated with respect to communication from the measuring room 19 into the control room 23. Communication between the patient 15 and the medical operator may be prevented in the case of a deactivation.

An emergency mode, however, continues to be activated during the deactivation. The patient 15 may inform the medical operator in the event of an emergency in the emergency mode. A transmission of image signals (e.g., video signals) for monitoring the patient 15 inside the patient-receiving region 14 during the magnetic resonance measurement may still also be maintained between the measuring room 19 and the control room 23 independently of an adjustment of a volume level, so the safety of the patient during the magnetic resonance scan is still provided.

The reduction in the volume level may include a reduction in a sensitivity (e.g., a volume sensitivity) of the first microphone 101 and/or a reduction in a volume level of the first loudspeaker 103. Activation of the volume level includes, for example, a setting of the volume level to an original value that this assumed before the deactivation and/or muting.

Alternatively or additionally, the volume level may be adjusted by the volume adjustment unit 106 during act 200 of detection of the communication signals by the first microphone 101 and/or during the act 202 of acoustic output of the communication signals by the first loudspeaker 103, as a function of an ambient volume level. The ambient volume level may be detected by a volume measurement and then be adjusted by the volume adjustment unit 106 as a function of the detected and/or measured ambient volume level of the volume level during the first method act 200 of detection of the communication signals by the first microphone 101 and/or during the act 202 of acoustic output of the communication signals by the first loudspeaker 103.

For example, the volume level may occur by the volume adjustment unit 106 as a function of a relation of the measured ambient volume level with respect to at least one reference value and/or threshold value. The volume level is automatically adjusted by the volume adjustment unit 106 during the act 200 of detection of the communication signals by the first microphone 101 and/or during the act 202 of acoustic output of the communication signals by the first loudspeaker 103 in the event of the reference value and/or threshold value being exceeded by the measured ambient volume level. The volume level may be automatically adjusted by the volume adjustment unit 106 in the event of the measured ambient volume level falling below the reference value and/or threshold value during the act 200 of detection of the communication signals by the first microphone 101 and/or during the act 202 of acoustic output of the communication signals by the first loudspeaker 103.

Two or more reference values and/or threshold values may be available for the adjustment of the volume level. The volume level may, for example, be adjusted gradually to the ambient volume in this connection.

The adjustment by the volume adjustment unit 106 may include a reduction in the volume level and/or a deactivation of the volume level. The reduction in the volume level may include a reduction in a sensitivity (e.g., a volume sensitivity) of the first microphone 101 and/or a reduction in a volume level of the first loudspeaker 103. The first microphone 101 and/or the first loudspeaker 103 is/are muted, for example, by the volume adjustment unit 106 by the deactivation of the volume level. The volume level may be set to its original value by the volume adjustment unit 106 and/or is activated again if the measured ambient volume level falls below the reference value and/or threshold value. For this purpose, the volume measurement occurs continuously throughout the entire magnetic resonance scan.

To detect the ambient volume, the communications unit 100 includes a separate volume detection unit 107 that, in the present exemplary embodiment, is arranged in the vicinity of the patient 15, since in the vicinity of the patient (e.g., in the vicinity of the magnetic unit 11), the loud interference noises may be produced by switching of the gradient coils. In the present exemplary embodiment, the volume detection unit 107 is arranged directly next to the first microphone 101, so the volume of the surroundings that acts on the first microphone 101 may be detected by the volume detection unit 106. Alternatively or additionally, the first microphone 101 may also be used for the detection of the ambient volume level. In an alternative or additional embodiment, the volume detection unit 107 may also be arranged inside the control room 23.

Alternatively or additionally, the ambient volume level may also be calculated for the magnetic resonance scan. The ambient volume level may be calculated, for example, using a gradient waveform for an adjusted gradient sequence of the magnetic resonance scan (e.g., the pending magnetic resonance scan), so even at the beginning of the magnetic resonance scan, there is a current ambient volume level available for the magnetic resonance scan for the adjustment of the volume level. The ambient volume level is calculated by the volume adjustment unit 106. The volume level is adjusted during the act 200 of detection of the communication signals by the first microphone 101 and/or during the act 202 of acoustic output of the communication signals by the first loudspeaker 103 analogously to the description of the adjustment of the volume level to a measured and/or detected ambient volume level stated above.

Although the invention has been illustrated and described in detail by the exemplary embodiments, the invention is not restricted by the disclosed examples. A person skilled in the art may derive other variations herefrom without departing from the scope of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for adjusting a volume level of a communications unit, wherein the communications unit is configured for communication between a medical operator and a patient during a magnetic resonance examination and wherein the communications unit comprises at least one microphone, at least one loudspeaker, and a control unit, the method comprising:
   detecting, by the at least one microphone, communication signals;
   measuring an ambient volume level by a volume measurement;
   transmitting the detected communication signals to the control unit;
   automatically adjusting a volume level of the at least one microphone or the at least one loudspeaker using the detected communication signals and the measured ambient volume level; and
   outputting, by the at least one loudspeaker, an acoustic output of the detected communication signal at the adjusted volume level.

2. The method of claim 1, wherein the communications unit is further configured to adjust the volume level as a function of a time parameter of a magnetic resonance scan.

3. The method of claim 1, wherein the the ambient volume level is measured by the at least one microphone.

4. The method of claim 1, wherein the the ambient volume level is measured by a separate volume detection unit of the communications unit.

5. The method of claim 1, wherein the automatic adjusting comprises a deactivation of the volume level.

6. The method of claim 1, wherein the automatic adjusting comprises an adjustment of the volume level to an ambient noise volume level of the at least one microphone or of the at least one loudspeaker.

7. The method of claim 1, wherein after a cessation of interference noises, after an end of a magnetic resonance scan, or after a cessation of interference noises and after an end of a magnetic resonance scan, the volume level is automatically set, by the communications unit, to an original volume level.

8. A communications unit comprising:
   at least one microphone;
   at least one loudspeaker; and
   a control unit,
   wherein the communications unit is configured for communication between a medical operator and a patient during a magnetic resonance examination,
   wherein the control unit comprises a volume adjustment unit configured to adjust a volume level of the communications unit, and
   wherein the communications unit is configured to:
      detect, by the at least one microphone, of communication signals;
      measure an ambient volume level by a volume measurement;
      transmit the detected communication signals to the control unit;
      automatically adjust a volume level of the at least one microphone or the at least one loudspeaker using the detected communication signals and the measured ambient volume level; and
      output an acoustic output of the detected communication signal at the adjusted volume level.

9. The communications unit of claim 8, the communications unit further comprising a volume detection unit configured to measure the ambient volume level.

10. A magnetic resonance device comprising:
    a communications unit comprising:
       at least one microphone;
       at least one loudspeaker; and
       a control unit,
    wherein the communications unit is configured for communication between a medical operator and a patient during a magnetic resonance examination,
    wherein the control unit comprises a volume adjustment unit configured to adjust a volume level of the communications unit, and
    wherein the communications unit is configured to:
       detect, by the at least one microphone, of communication signals;
       measure an ambient volume level by a volume measurement;
       transmit the detected communication signals to the control unit;
       automatically adjust a volume level of the at least one microphone or the at least one loudspeaker using the detected communication signals and the measured ambient volume level; and
       output an acoustic output of the detected communication signal at the adjusted volume level.

11. In a non-transitory computer-readable storage medium including instructions executable by one or more processors to adjust a volume of a communications unit, wherein the communications unit is configured for communication between a medical operator and a patient during a magnetic resonance examination and comprises at least one microphone, at least one loudspeaker, and a control unit, the instructions comprising:
    detect, by the at least one microphone, communication signals;
    measure an ambient volume level by a volume measurement;
    transmit the detected communication signals to the control unit;
    automatically adjust a volume level of the at least one microphone or the at least one loudspeaker using the detected communication signals and the measured ambient volume level; and
    output an acoustic output of the detected communication signal at the adjusted volume level.

12. The non-transitory computer-readable storage medium of claim 11, wherein the communications unit is further configured to adjust the volume level as a function of a time parameter of a magnetic resonance scan.

13. The non-transitory computer-readable storage medium of claim 11, wherein the ambient volume level is measured by the at least one microphone.

14. The non-transitory computer-readable storage medium of claim 11, wherein the ambient volume level is measured by a separate volume detection unit of the communications unit.

15. The non-transitory computer-readable storage medium of claim 11, wherein the automatic adjustment comprises a deactivation of the volume level.

\* \* \* \* \*